(12) United States Patent
Jurick et al.

(10) Patent No.: US 12,376,893 B2
(45) Date of Patent: Aug. 5, 2025

(54) ORTHOPAEDIC IMPLANT WITH FIXATION FEATURE AND A METHOD OF IMPLANTING THEREOF

(71) Applicant: SMed-TA/TD, LLC, Columbia City, IN (US)

(72) Inventors: Joseph W. Jurick, Fort Wayne, IN (US); Steven Dietzel, Warsaw, IN (US); Gregory C. Stalcup, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 173 days.

(21) Appl. No.: 16/855,199

(22) Filed: Apr. 22, 2020

(65) Prior Publication Data

US 2020/0246051 A1      Aug. 6, 2020

Related U.S. Application Data

(62) Division of application No. 15/833,259, filed on Dec. 6, 2017, now Pat. No. 10,631,904.

(60) Provisional application No. 62/430,585, filed on Dec. 6, 2016.

(51) Int. Cl.
*A61F 2/38* (2006.01)
*A61B 17/86* (2006.01)
*A61F 2/30* (2006.01)
*A61B 17/88* (2006.01)

(52) U.S. Cl.
CPC .......... *A61B 17/86* (2013.01); *A61F 2/30771* (2013.01); *A61F 2/389* (2013.01); *A61B 17/8872* (2013.01); *A61F 2002/30187* (2013.01); *A61F 2002/30212* (2013.01); *A61F 2002/30579* (2013.01); *A61F 2002/30879* (2013.01); *A61F 2002/30892* (2013.01); *A61F 2002/3895* (2013.01); *A61F 2310/00023* (2013.01)

(58) Field of Classification Search
CPC ............ A61F 2/3859–389; A61F 2002/30579
See application file for complete search history.

(56) References Cited

U.S. PATENT DOCUMENTS

| | | | | | |
|---|---|---|---|---|---|
| 4,479,271 | A | * | 10/1984 | Bolesky | B22F 7/002 623/20.17 |
| 4,769,039 | A | * | 9/1988 | Horber | A61F 2/389 623/20.32 |
| 4,808,185 | A | * | 2/1989 | Penenberg | A61B 17/1624 623/20.29 |
| 4,919,671 | A | * | 4/1990 | Karpf | A61F 2/389 623/20.32 |

(Continued)

*Primary Examiner* — Eduardo C Robert
*Assistant Examiner* — Steven J Cotroneo
(74) *Attorney, Agent, or Firm* — TAYLOR & EDELSTEIN, PC

(57) ABSTRACT

An orthopaedic implant includes an implant body having a first surface and a second surface opposite the first surface. The second surface includes a fixation feature. The fixation feature is configured to have a variable width for fastening the implant to a fixation bore formed in a bone. The implant body is D-shaped and has a straight edge and a curved edge. A length of the fixation feature is substantially parallel to the straight edge of the implant body. The fixation feature is configured to have a width that tapers along the length of the fixation feature.

9 Claims, 12 Drawing Sheets

(56) References Cited

U.S. PATENT DOCUMENTS

| | | | | |
|---|---|---|---|---|
| 5,702,447 | A | * | 12/1997 | Walch ............... A61F 2/4081 606/327 |
| 5,782,924 | A | * | 7/1998 | Johnson ............ A61F 2/4081 623/18.11 |
| 6,102,954 | A | * | 8/2000 | Albrektsson ....... A61B 17/8625 623/20.32 |
| 6,905,513 | B1 | * | 6/2005 | Metzger ............... A61F 2/08 623/20.14 |
| 6,966,928 | B2 | * | 11/2005 | Fell ..................... A61F 2/38 623/14.12 |
| 7,572,293 | B2 | * | 8/2009 | Rhodes ............... A61F 2/389 623/20.32 |
| 8,192,491 | B2 | * | 6/2012 | Fox .................... A61L 27/18 623/14.12 |
| 8,540,778 | B2 | * | 9/2013 | Rhodes ............... A61F 2/389 623/20.32 |
| 8,709,091 | B2 | | 4/2014 | Rhodes et al. |
| 8,764,839 | B2 | * | 7/2014 | Rhodes ............... A61F 2/389 623/20.32 |
| 9,655,730 | B2 | * | 5/2017 | Fox .................... A61L 27/18 |
| 10,194,963 | B2 | * | 2/2019 | Stalcup ............. A61B 17/864 |
| 2002/0022890 | A1 | * | 2/2002 | Jacobsson .......... A61F 2/389 623/20.14 |
| 2007/0129808 | A1 | * | 6/2007 | Justin ................. A61F 2/389 623/22.36 |
| 2010/0249941 | A1 | * | 9/2010 | Fell .................... A61F 2/3836 623/20.28 |
| 2012/0123553 | A1 | * | 5/2012 | Sidebotham ........ A61F 2/3601 623/18.11 |
| 2016/0113696 | A1 | | 4/2016 | Stalcup et al. |
| 2022/0000629 | A1 | * | 1/2022 | Mehta ................ A61F 2/30771 |

* cited by examiner

ORTHOPAEDIC IMPLANT WITH FIXATION FEATURE AND A METHOD OF IMPLANTING THEREOF

CROSS REFERENCE TO RELATED APPLICATIONS

This is a division of U.S. patent application Ser. No. 15/833,259, entitled "ORTHOPAEDIC IMPLANT WITH FIXATION FEATURE AND A METHOD OF IMPLANTING THEREOF," filed Dec. 6, 2017, which is incorporated herein by reference. U.S. patent application Ser. No. 15/833,259 is a non-provisional application based upon U.S. provisional patent application Ser. No. 62/430,585, entitled "ORTHOPAEDIC IMPLANT WITH FIXATION FEATURE AND A METHOD OF IMPLANTING THEREOF," filed Dec. 6, 2016, which is incorporated herein by reference.

FIELD OF THE INVENTION

The present invention relates to orthopaedic implants, and particularly to orthopaedic implants with variable width fixation features and methods of implanting thereof.

BACKGROUND OF THE INVENTION

Conventional orthopaedic implants are typically secured to tissue at the implantation site via known orthopaedic fastening devices, such as bone screws and/or pins. Although implants secured in such a manner typically do not become loose, there may exist unnecessary stress on conventional fastening devices due to internal forces produced by surrounding tissue, as well as due to external forces that may be produced by various, everyday patient activities. Such external forces may be easily transferred via structures of the body to the implantation site.

Furthermore, the number of conventional fastening devices used to securely fasten an implant may be such as to damage the surrounding tissue, or it may be that the implantation site does not offer enough potential locations for receiving the number of bone screws and/or pins required to securely fasten the implant.

What is needed in the art is a way to fixate orthopaedic implants to bone tissue that overcomes some of the described disadvantages present in the art.

SUMMARY OF THE INVENTION

In some exemplary embodiments disclosed herein, there is provided an orthopaedic implant including an implant body having a first surface and a second surface opposite the first surface. The second surface includes a fixation feature. The fixation feature is configured to have a variable width for fastening the implant to a fixation bore formed in a bone. The implant body is D-shaped and has a straight edge and a curved edge. A length of the fixation feature is substantially parallel to the straight edge of the implant body. The fixation feature is configured to have a width that tapers along the length of the fixation feature.

In some exemplary embodiments disclosed herein, a method for implanting an orthopaedic implant includes: forming a resected surface in a bone of a patient; forming a fixation bore in the resected surface; implanting the orthopaedic implant, the orthopaedic implant including an implant body having a first surface and a second surface opposite the first surface, the second surface including a fixation feature, the fixation feature being configured to have a variable width; and pressing the fixation feature of the implant into the fixation bore.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
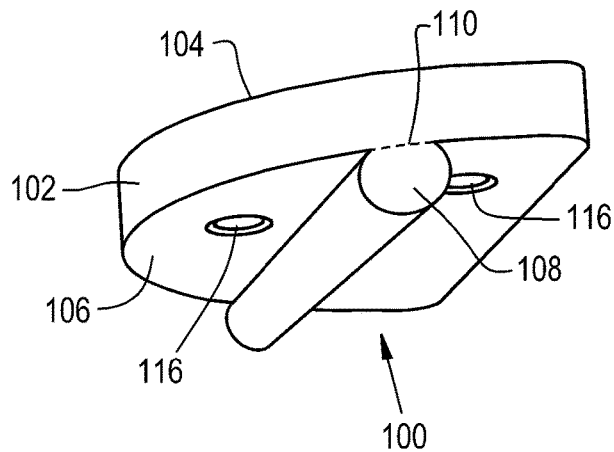
FIG. 1 is a first perspective view of an orthopaedic implant, according to an embodiment of the invention.
Figure 2:
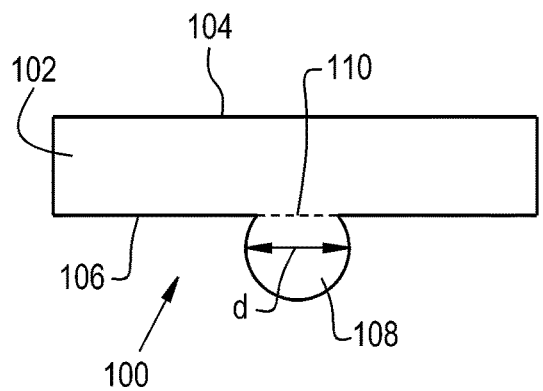
FIG. 2 is a second perspective view of the orthopaedic implant of FIG. 1, according to an embodiment of the invention.
Figure 3:
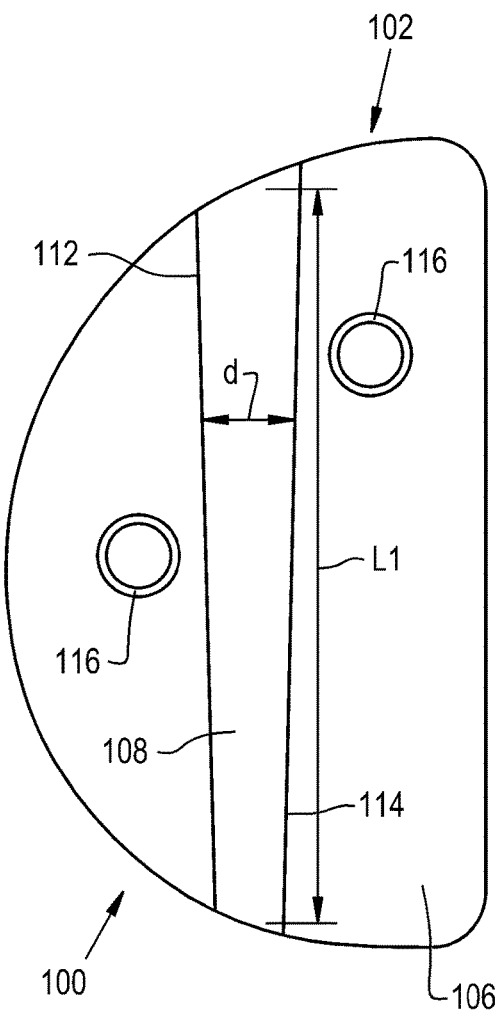
FIG. 3 a third perspective view of the orthopaedic implant of FIG. 1, according to an embodiment of the invention.

Referring to the drawings, and more particularly to FIGS. 1-3, there is shown different perspective views of an embodiment of an orthopaedic implant 100 which generally includes an implant body 102 shaped and configured for implantation within a body of a patient (not shown). The implant body 102 shown in FIGS. 1-3 is configured for implantation in a tibia, as shown further herein, and thus is substantially shaped as a D-shape, which can be seen in FIG. 3. As the implant body 102 will be implanted within a patient, the implant body 102 may comprise one or more biocompatible materials suitable for short or long-term placement within an animal body, human or otherwise, which can include, but are not limited to: metals such as titanium, stainless steel, cobalt chrome, and/or tantalum; polymers such as ultra-high molecular weight polyethylene (UHMWPE), other forms of polyethylene, polyether ether ketone (PEEK), polylactic acid (PLA), and/or polyglycolic acid (PGA); and/or ceramics such as hydroxyapatite (HA), high-density alumina, so-called "Bioglass," and graphite. It should be appreciated that all of the previously mentioned materials are exemplary only, and many other types of biomaterials can be incorporated in the implant body 102 formed according to embodiments of the present invention.

Figure 4:
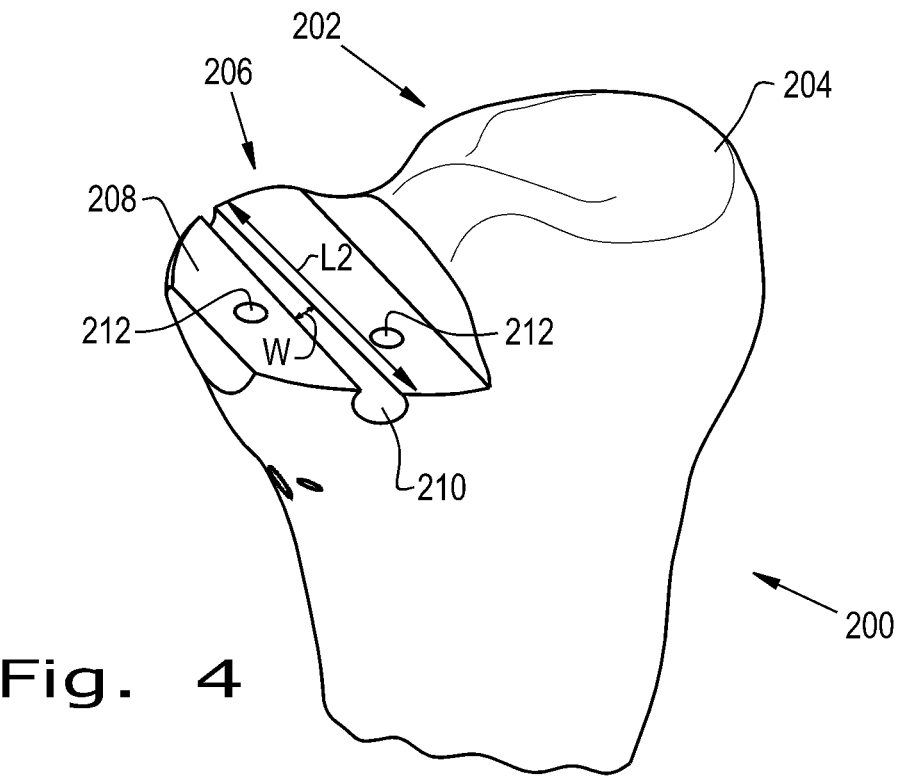
FIG. 4 is a tibia of a patient, prepared for receiving the implant of FIGS. 1-3, according to an embodiment of the invention.

The implant body 102 includes a first surface 104 which, when implanted, may articulate against a head of the patient's femur, or a head of a femoral implant, and a second surface 106 opposite the first surface 104. The first surface 104 may also be referred to as a "top surface," which may be an articulating surface, and the second surface 106 may be referred to as a "bottom surface." The bottom surface 106 of the implant body 102 includes a fixation feature 108 which will press fit into a fixation bore 210 (FIG. 4) formed in the patient's tibia 200 (FIG. 4). The fixation feature 108 can be formed to have a substantially peg-like shape, as shown in FIG. 2, except for a boundary portion 110 of the fixation feature 108 defining where the fixation feature 108 meets the bottom surface 106 of the implant body 102, where the shape of the fixation feature 108 flattens. The fixation feature 108 can be integrally formed in the implant body 102 by, for example, molding or the fixation feature 108 can be formed as a separate piece which is then attached to the bottom surface 106 of the implant body 102 by, for example, welding. It should be appreciated that the previously described methods of manufacturing the implant body 102 with the fixation feature are exemplary only, and the implant body 102 with the fixation feature 108 can be formed according to any suitable manufacturing method.

Referring specifically to FIG. 3, it can be seen that the fixation feature 108 comprises a variable width. For example, the fixation feature 108 can define a plurality of widths or, in the case of the fixation feature having a rounded shape, a plurality of diameters d, where the widths or diameters are measured from one lateral side 112 of the fixation 108 to an opposite lateral side 114. In this sense, the width or diameter d of the fixation feature 108 tapers along a length L1 of the fixation feature 108, the significance of which will be further described herein. To provide additional fixation during implantation, the implant body 102 can also have one or more screw openings 116 formed therein which are shaped to accept an orthopaedic screw which will be driven into a surface of the tibia.

Referring now to FIG. 4, a prepared tibia 200 of a patient is shown after being prepared for implantation of the implant 100 shown in FIGS. 1-3. As shown, the tibia 200 has a tibia head 202 comprising an intact head 204 and a resected head 206 having a resected surface 208 in the tibia 200 where the implant 100 will be implanted. After resecting the tibia 200 to form the resected head 206 including the resected surface 208, a fixation bore 210 is formed in the resected surface 208 where the fixation feature 108 will be placed to implant the implant body 102 and fixate the implant 100 to the tibia 200. The fixation bore 210 can be formed having either a uniform width w or a width w tapered along a length L2 of the fixation bore 210, the significance of which will be described further herein. Additionally, one or more pilot holes 212 can be formed in the resected surface 208 or on other parts of the tibia 200 to accept bone screws (not shown) to fixate the implant body 102 to the tibia 200, as previously described. Other holes (not shown) can also be formed in the tibia 200 to allow for a suture (not shown) to connect to the bottom surface 106 of the implant body 102 and pull the implant 100 into the resected surface 208, providing further fixation, as illustrated further below in conjunction with FIGS. 7-11. Such a method is described in U.S. Patent Application Publication No. 2016/0113696 to Stalcup et al., which is incorporated herein by reference. Further, while the bottom surface 106 of the implant body 102 is shown bare, an ingrowth material (not shown) can be attached to the bottom surface 106 to promote tissue ingrowth into the ingrowth material to provide additional fixation to the implant 100. Such ingrowth materials are known and can include, but are not limited to various porous metals, polymers, and/or ceramics. Additionally, if the bottom surface 106 of the implant body 102 is porous, the pores of the material can be filled with one or more bioactive substances to further encourage bone ingrowth such as growth factors, anti-inflammatories, antibiotics, painkillers, etc. It should therefore be appreciated that any ingrowth material attached to the bottom surface 106 of the implant body 102 can be tailored to achieve specific design criteria and be utilized according to the present invention.

Figure 5:
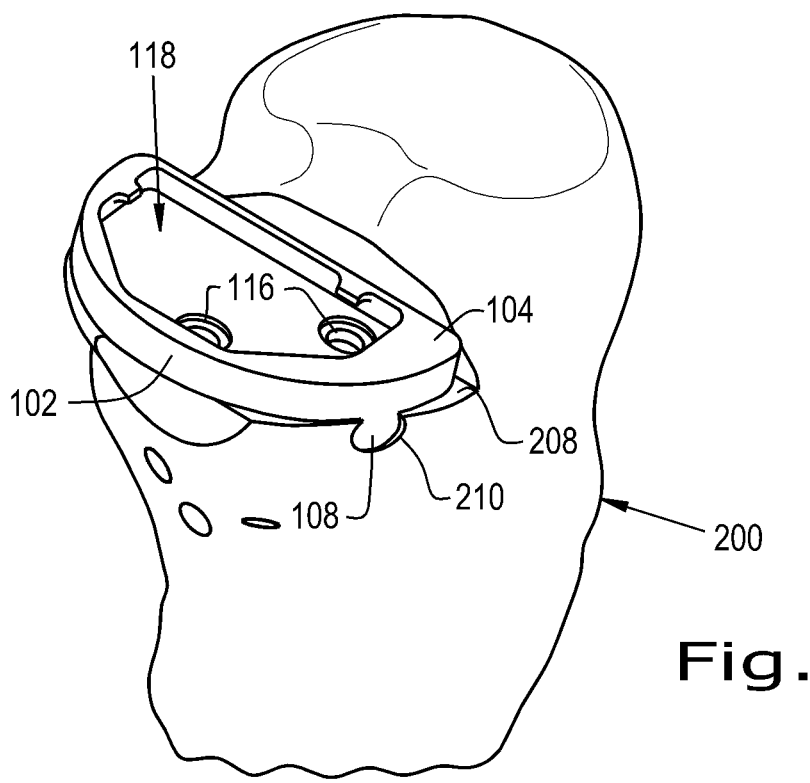
FIG. 5 is a first perspective view of the implant body shown in FIGS. 1-3 implanted in the prepared tibia shown in FIG. 4, according to an embodiment of the invention.
Figure 6:
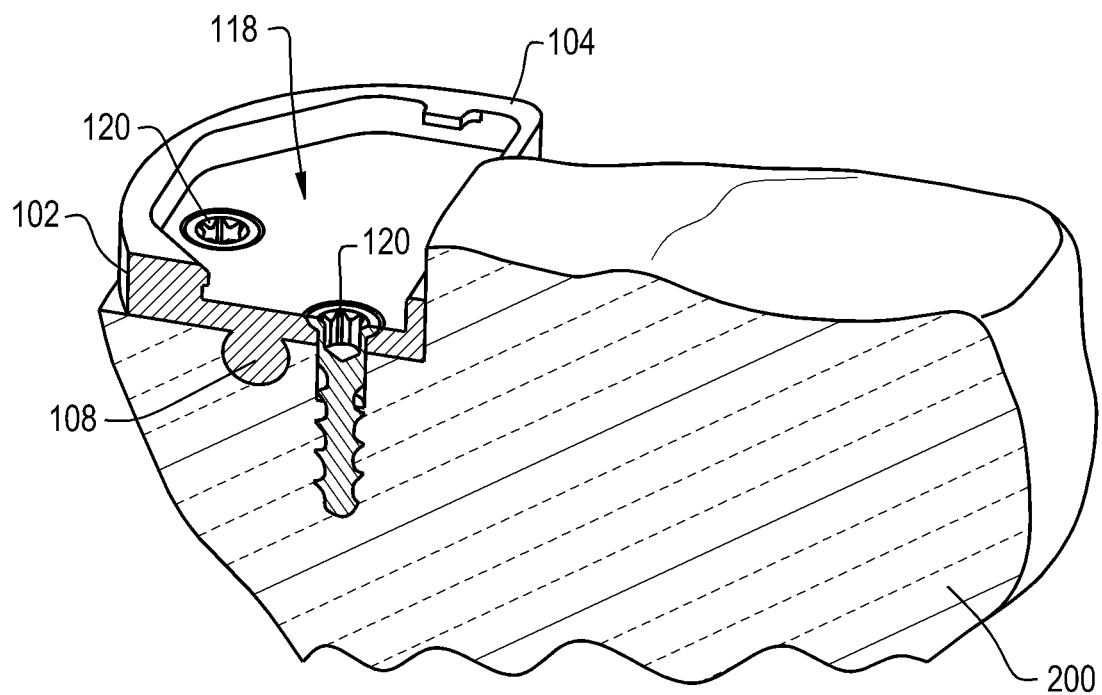
FIG. 6 is a second perspective view of the implant body shown in FIGS. 1-3 implanted in the prepared tibia shown in FIG. 4, according to an embodiment of the invention.
Figure 7:
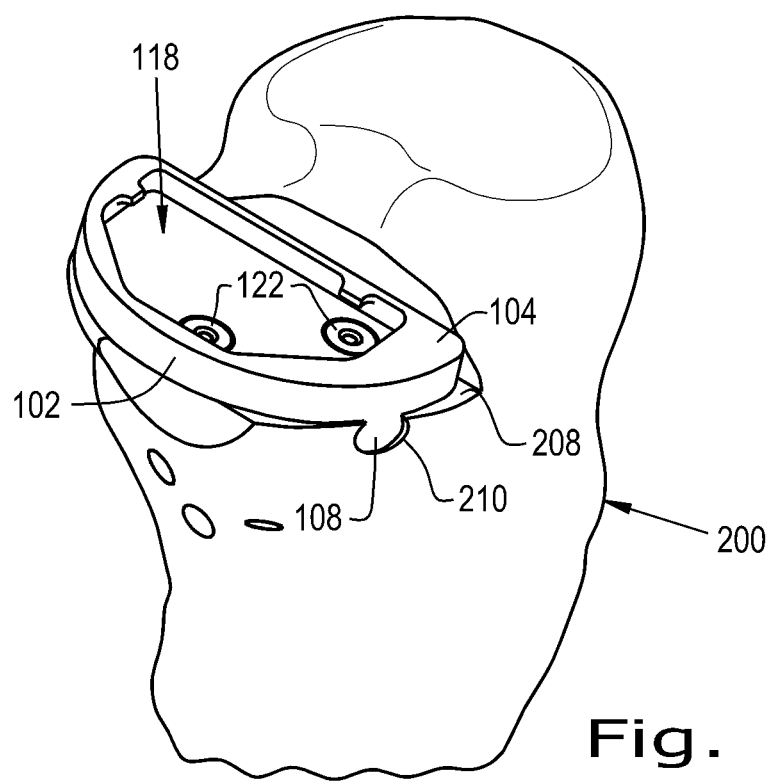
FIG. 7 is a third perspective view of the implant body shown in FIGS. 1-3 implanted in the prepared tibia shown in FIG. 4, according to an embodiment of the invention.
Figure 8:
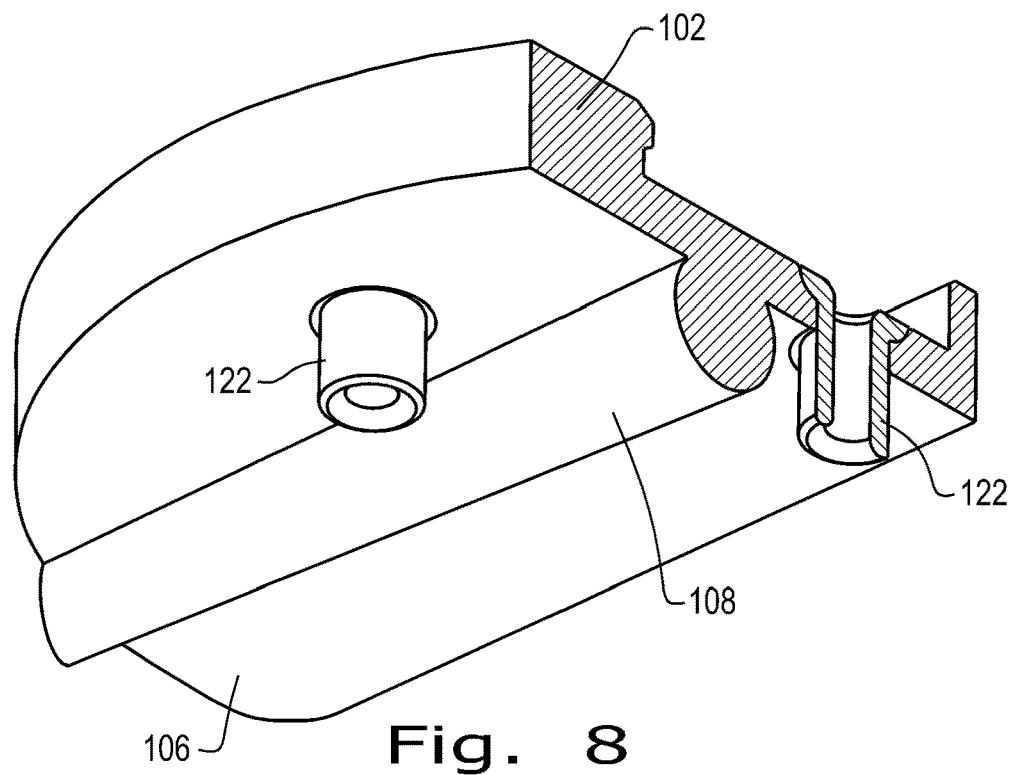
FIG. 8 is a first perspective view of an orthopaedic implant of FIGS. 1-3 showing suture anchors, according to an embodiment of the invention.
Figure 9:
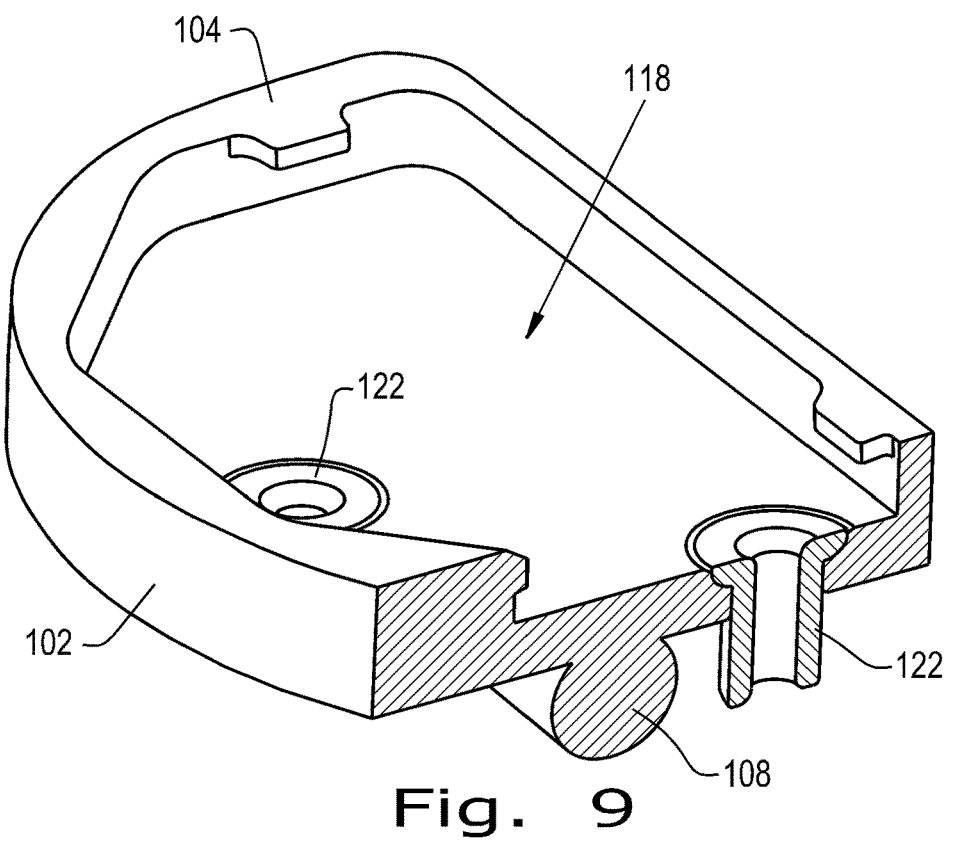
FIG. 9 is a second perspective view of an orthopaedic implant of FIGS. 1-3 showing suture anchors, according to an embodiment of the invention.
Figure 10:
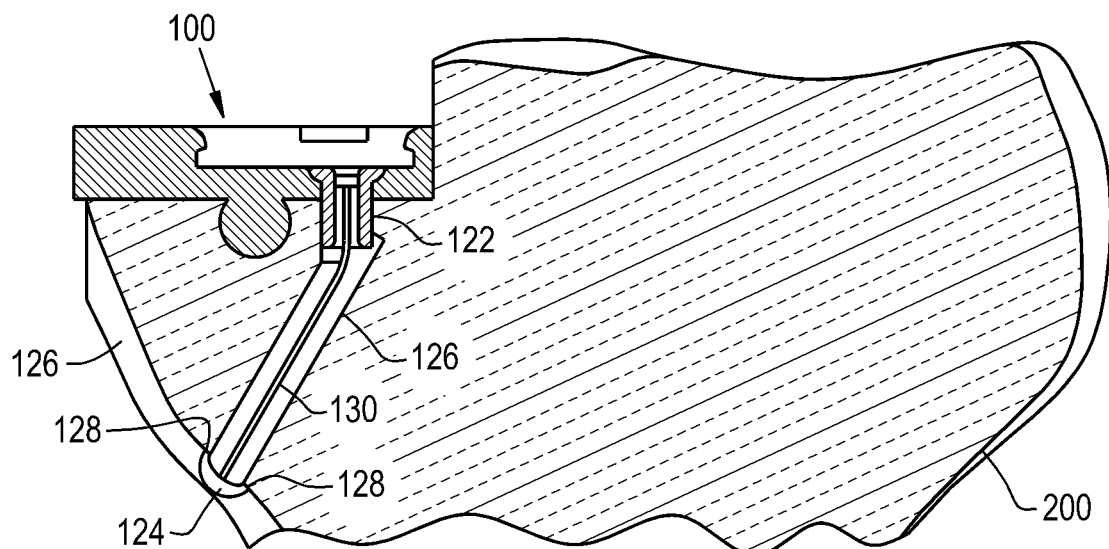
FIG. 10 is the orthopaedic implant shown in FIGS. 8-9, implanted in the prepared tibia of FIG. 4, illustrating anterior suture channels, according to an embodiment of the invention.
Figure 11:
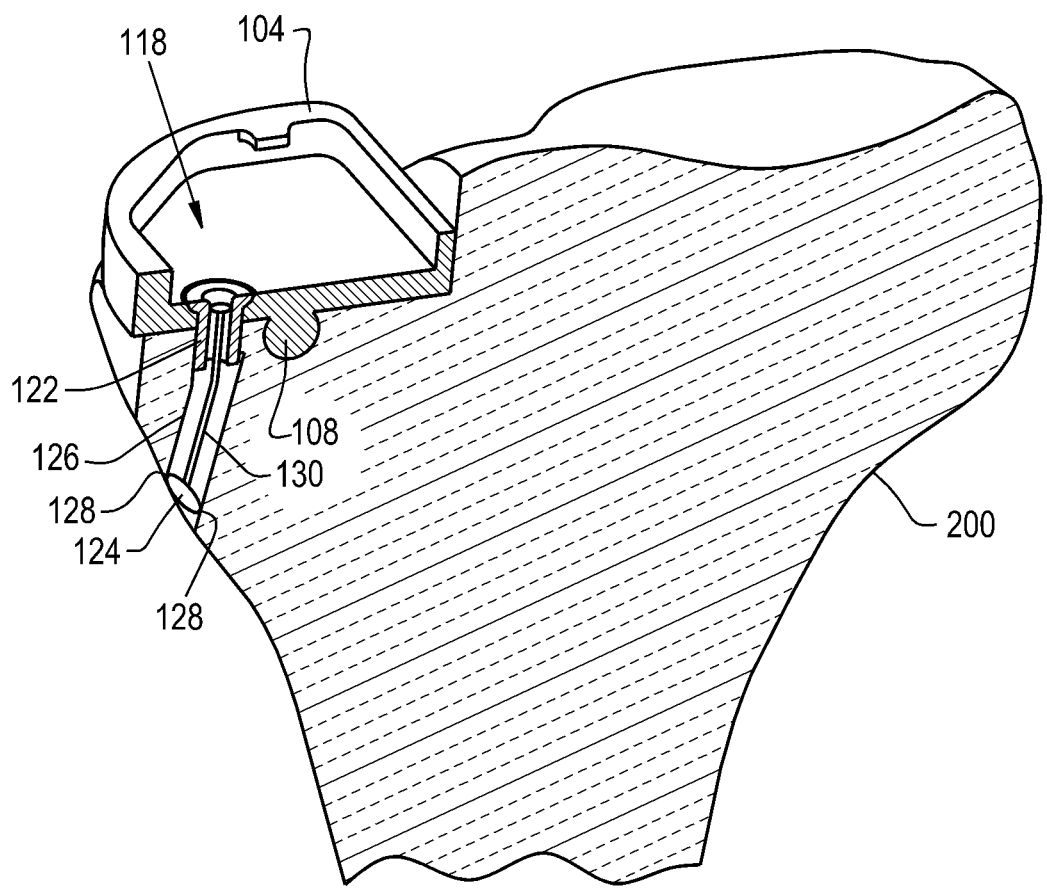
FIG. 11 is the orthopaedic implant shown in FIGS. 8-9, implanted in the prepared tibia of FIG. 4, illustrating posterior suture channels, according to an embodiment of the invention.

Referring now to FIGS. 5-6, the implant body 102 shown in FIGS. 1-3 is shown implanted in the prepared tibia 200 shown in FIG. 4. As can be seen, the fixation feature 108 of the implant body 102 has been pressed into the fixation bore 210 formed in the resected surface 208 to provide additional fixation of the implant body 102 to the tibia 200, especially in directions which are perpendicular to the length L1 (see FIG. 3) of the fixation feature 108. As is known, cancellous bone tissue, as opposed to cortical bone tissue, is fairly spongey and compliant. By forming the fixation feature 108 to have a portion with widths less than widths of a portion of the fixation bore 210, and to have widths at positions along the length L1 of at least a portion of the fixation feature 108 equal or greater than the widths at corresponding positions along the length L2 of the fixation bore 210, a smallest width of the fixation feature 108 can be inserted into the fixation bore 210 and the implant 100 then slid so the fixation feature 108 completely fills the fixation bore 210. Due to the compliant nature of cancellous bone tissue, the tissue forming the boundaries of the fixation bore 210 can expand in response to the tapering width of the fixation feature 108 being pressed (e.g., slid) into the fixation bore 210. This allows the fixation feature 108 to gradually expand the width of the fixation bore 210 as the fixation feature 108 is inserted into the fixation bore 210, preventing sudden expansion of the fixation bore 210 that could result in a stress fracture in the bone tissue of the tibia 200, or in any bone tissue into which the implant 100 is implanted. By sizing the fixation bore 210 relative to the fixation feature 108 in this manner, the resistive compression forces of the bone tissue to the expansion caused by inserting the fixation feature 108 into the fixation bore 210 can help to hold the implant body 102 within the tibia 200. Alternatively, if the fixation bore 210 is formed with a tapering width as well, the tapering width of the fixation bore 210 along a length L2 of the fixation bore 210 can be designed so the width of the fixation bore 210 is slightly less than corresponding widths of the fixation feature 108 where the fixation feature 108 will rest when the implant body 102 is implanted within the tibia 200. In this sense, the fixation feature 108 is still oversized in relation to the fixation bore 210, resulting in compressive force from the bone tissue holding the fixation feature 108 within the fixation bore 210. It should therefore be appreciated that the diameters or widths of the fixation feature 108 and/or the widths of the fixation bore 210 can be adjusted, as desired, so long as at least a portion of the fixation feature 108 has a greater diameter or width than a width of any portion of the fixation bore 210.

As can be further seen in FIGS. 5-6, the implant body 102 can have a recess 118 formed in the top surface 104 which can accept an articulating insert (not shown) that the femoral head (not shown), or femoral head replacement (not shown), will articulate against following implantation. By having a removable articulating insert rather than a formed articulating surface, orthopaedic screws 120 (i.e., also referred to as bone screws) can be inserted through the screw openings 116 formed in the implant body 102 without damaging or protruding from the articulating surface.

Alternatively, as shown in FIGS. 7-11, one or more of the openings 116 formed in the implant body 102 can house a suture anchor 122 that will connect to a tensioning member, such as an anchored suture 124, residing in a suture channel 126 formed in the tibia 200. A suture 130, once attached to the suture anchor 122, can be anchored to the tibia 200 by, for example, wrapping around a button (e.g., the anchored suture 124) that presses against a surface 128 of the tibia 200 adjacent the suture channel 126, and can be placed on an anterior side (FIG. 10) and/or posterior side (FIG. 11) of the tibia 200. Such methods of anchoring a tensioning member to a bone and utilizing tension, via the suture 130, from the anchored tensioning member to fixate an implant 100 are taught by Stalcup et al., as previously referenced, and therefore further description is omitted for the sake of brevity.

Figure 12:
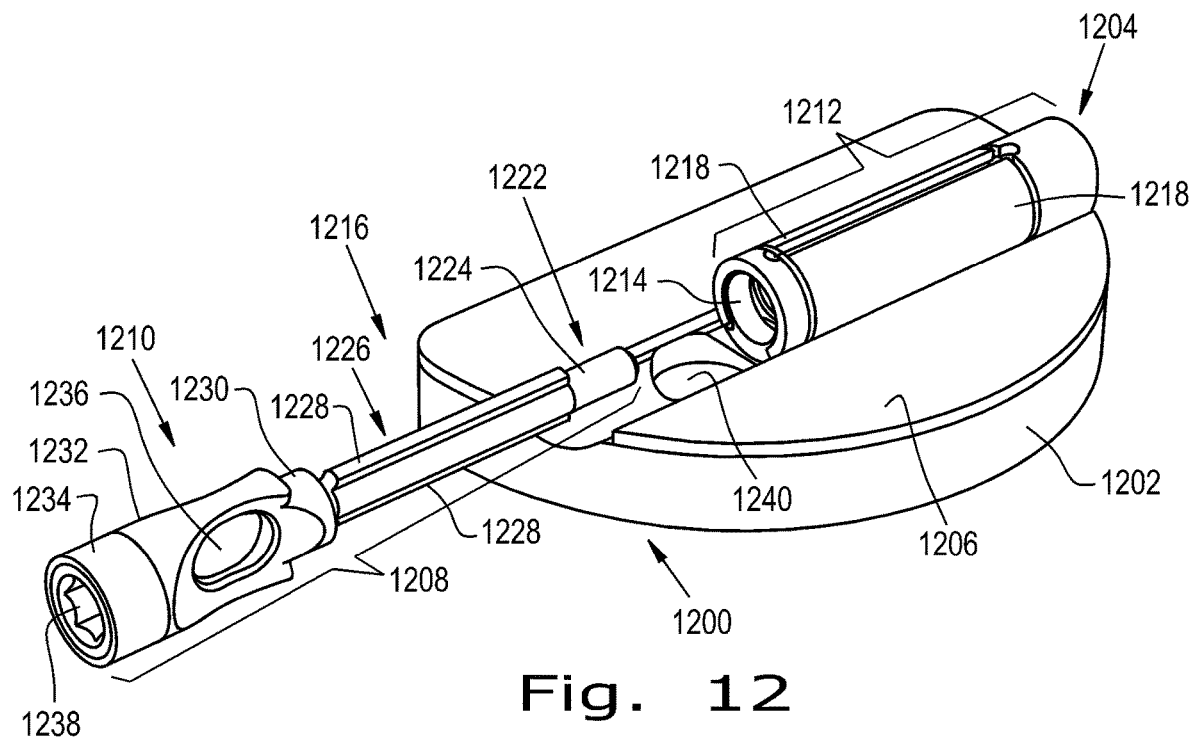
FIG. 12 is a first perspective view of an orthopaedic implant, according to another embodiment of the invention.

Referring now to FIG. 12, another embodiment of an orthopaedic implant 1200 formed according to the present invention is shown which includes an implant body 1202 having a fixation feature 1204 on a bottom surface 1206 of the implant body 1202. As will be seen further below, the fixation feature 1204 is configured to have a variable width. As can be seen, the implant body 1202 shown in FIG. 12 is formed as a tibial implant, but can be formed in other shapes as well. The implant body 1202 of the implant 1200 shown in FIG. 12, therefore, can be formed similarly to the previously described implant body 102, with differences described further herein. As shown, the bottom surface 1206 and fixation feature 1204 of the implant body 1202 can be partially or fully covered with an ingrowth material to promote tissue ingrowth, similar to the previously described ingrowth material.

Figure 16:
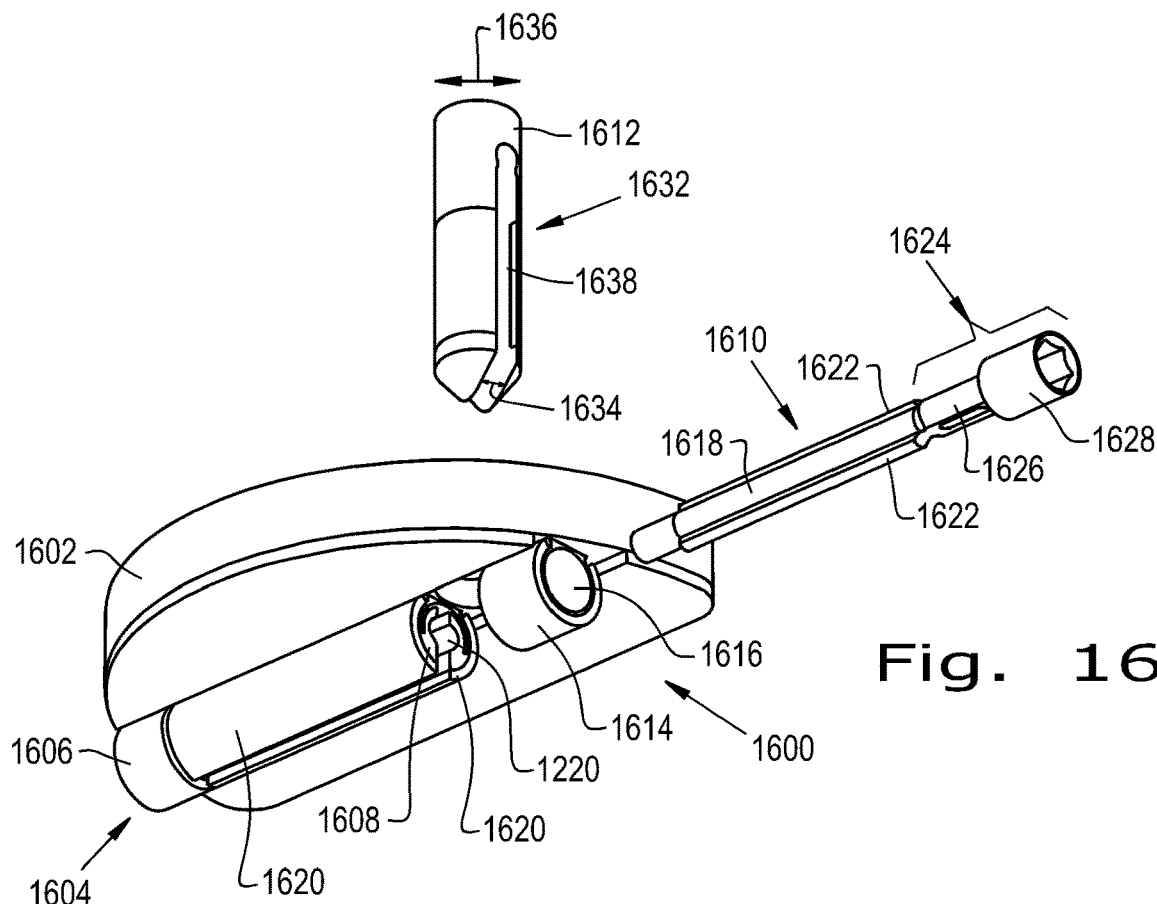
FIG. 16 is a first perspective view of an orthopaedic implant, according to yet another embodiment of the invention.

Unlike the implant body 102 previously described and shown, the implant body 1202 shown in FIG. 12 has an expandable feature that does not have an entirely set width. In the FIG. 12 embodiment, the fixation feature 1204 is formed as a cylinder which has an expander portion 1208 having an end segment 1210 with a constant end diameter, or width if the fixation feature does not have a substantially circular cross-section, and an expandable portion 1212 configured to receive the expander portion 1208. The expandable portion 1212 also includes an expansion bore 1214 which accommodates (i.e., receives) an insertion body 1216 of the expander portion 1208, which will be described further herein. As can be seen, the expandable portion 1212 has roughly the same diameter as the end segment 1210 of the expander portion 1208 when the insertion body 1216 of the expander portion 1208 is not placed within the expansion bore 1214. The expandable portion 1212 comprises one or more expandable parts 1218, also referred to as one or more expansion surfaces, coupled together to form a part of the cylinder comprising the expansion bore 1214 defined by inner surfaces (not shown) of the one or more expandable parts 1218 (i.e., one or expansion surfaces). While it cannot be seen in FIG. 12, the expandable portion 1212 has one or more cam surfaces 1220 (shown in FIG. 16) formed on a wall (i.e., formed on portions of the inner surfaces) defining a boundary of the expansion bore 1214, which will interact with the expander portion 1208 as described further herein. The expansion bore 1214 is formed along a longitudinal axis of the cylinder formed by the one or more expandable parts 1218.

As shown in FIG. 12, the insertion body 1216 of the expander portion 1208 will be placed in the expansion bore 1214 and the end segment 1210 of the expander portion 1208 will reside outside of the expansion bore 1214. The insertion body 1216 can have an end portion 1222 comprising a smooth tip 1224 with a constant radius which connects to a cam portion 1226 having cams 1228 on opposite sides of the insertion body 1216 which will interact with the cam surfaces 1220 of the expandable portion 1212, which is described further herein. The insertion body 1216 may connect to the end segment 1210 by an intermediate portion 1230 which can have a first diameter or width which is greater than the diameter or width of the insertion body 1216. The end segment 1210 can be connected to the intermediate portion 1230 and have a second diameter or width which is greater than the diameter or width of the intermediate portion 1230 and can be roughly equivalent to the diameter of the expandable portion 1212 of the fixation feature 1204, when non-expanded. The end segment 1210 comprises a locking portion 1232 and a keyed portion 1234. The locking portion 1232 can also have an opening 1236 formed therethrough which is formed through a pair of opposing surfaces in a direction which is transverse to the longitudinal axis of the expander portion 1208. In this sense, the cams 1228 formed on the insertion body 1216 can extend parallel to the longitudinal axis along a length of at least a portion of the insertion body 1216, the significance of which will be described further herein. The keyed portion 1234 is configured, via a socket 1238, for example, to allow a tool, such as a screwdriver, to rotate the expander portion 1208 and ingrowth material placed on one or more surfaces of the expander portion 1208.

Figure 13:
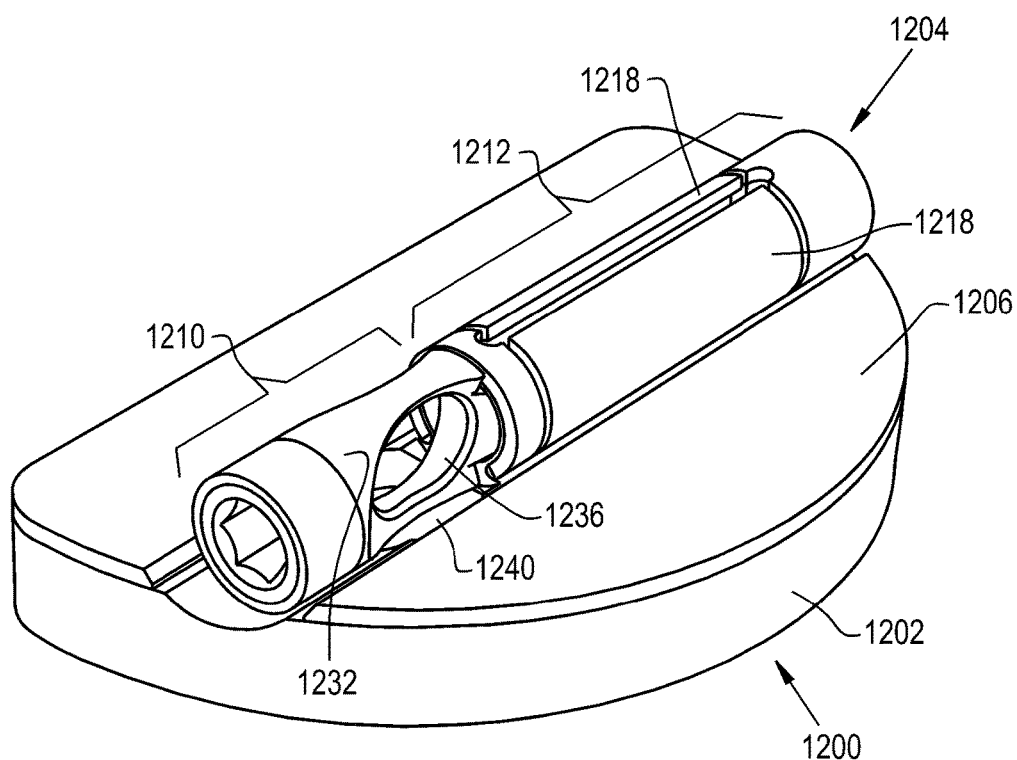
FIG. 13 is a second perspective view of the orthopaedic implant of FIG. 12, according to an embodiment of the invention.

Referring now to FIG. 13, the implant 1200 is shown with the insertion body 1216 of the expander portion 1208 placed within the expansion bore 1214 of the expandable portion 1212. As can be seen, the width of the expandable portion 1212 has not changed when the insertion body 1216 of the expander portion 1208 is placed in the expansion bore 1214 in the orientation shown, as the cams 1228 of the insertion body 1216 have not contacted the cam surfaces 1220 of the expandable portion 1212 to spread apart the one or more expandable parts 1218 (or as shown, spread apart two expandable halves 1218) of the expandable portion 1212. Further, the opening 1236 formed in the locking portion 1232 of the end segment 1210 is not aligned with a screw opening 1240 formed through the bottom surface 1206 of the implant body 1202, thereby preventing a bone screw (not shown) from extending through both openings to fixate the implant 1200.

Figure 14:
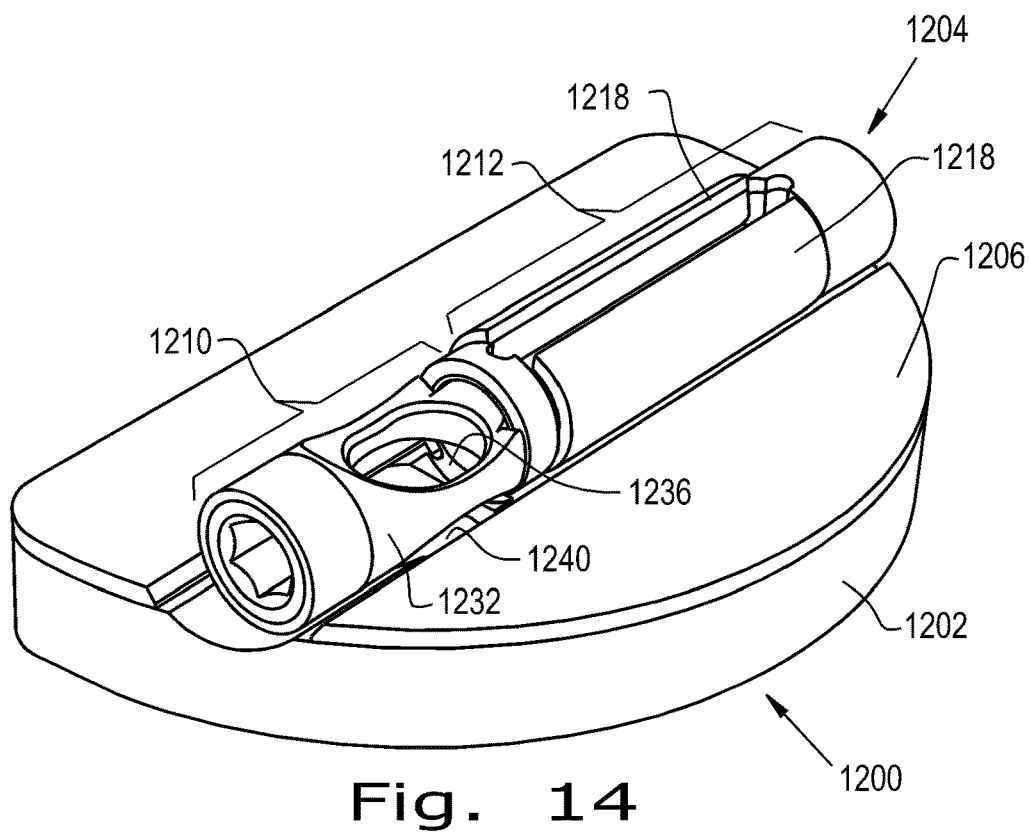
FIG. 14 a third perspective view of the orthopaedic implant of FIG. 12, according to an embodiment of the invention.

Referring now to FIG. 14, the implant 1200 is shown after the expander portion 1208 rotates 90° (or rotates to another pre-determined angle that is less than 90°) clockwise or counter-clockwise about the longitudinal axis, forcing the cams 1228 of the insertion body 1216 to contact the cam surfaces 1220 of the expandable portion 1212. As the cams 1228 of the insertion body 1216 travel across the cam surfaces 1220 of the two expandable halves 1218 of the expandable portion 1212, as in this exemplary embodiment, the force applied by the cams 1228 on the cam surfaces 1220 causes the two expandable halves 1218 to spread apart from one another, increasing the effective diameter or width of the expandable portion 1212 to an expanded diameter or width which is greater than the diameter or width of the end segment 1210 of the expander portion 1208 of the fixation feature 1204. The increase in the diameter or width of the expandable portion 1212, therefore, can depend on a thickness of the cams 1228 of the insertion body 1216 relative to the diameter or width of the insertion body 1216 of the expander portion 1208. While it is shown that the expandable portion 1212 has two expandable halves 1218 that are both spread apart when the expander portion 1208 is turned, it is contemplated that the expandable portion 1212 may only have a single expandable part that gets expanded from a stationary portion when the expander portion 1208 rotates. Similarly, it is also contemplated that the expandable portion 1212 may have more than the two expandable parts 1218 that are spread apart when the expander portion 1208 is turned. Therefore, it should be appreciated that the expandable portion 1212 can be configured in many different ways that allow turning of the expander portion 1208 to change the diameter or width of the expandable portion 1212 from a non-expanded diameter or width to an expanded diameter or width which is greater than the non-expanded diameter or width.

By expanding the diameter or width of the expandable portion 1212 of the implant body 1202, the implant body 1202 without the expander portion 1208 can be implanted with the fixation feature 1204 placed in a fixation bore, such as fixation bore 210, having a diameter or width which is equal to or slightly larger than the non-expanded diameter or width of the fixation feature 1204. Once the fixation feature 1204 is fully placed within the fixation bore 210 and the implant body 1202 without the expander portion 1208 is properly oriented at the implantation site, the expander portion 1208 can then be inserted in the expansion bore 1214 and rotated so the expandable portion 1212 expands to the expanded diameter or width, as shown in FIG. 14. This produces resistive compression forces from the surrounding bone tissue of the fixation bore 210 to help with fixating the implant body 1202. However, these same resistive compression forces from the bone tissue also tend to compress the expandable portion 1212 together, which can cause the expandable halves 1218 of the expandable portion 1212 to come together and rotate the expander portion 1208 in the process. Such an event presents a few negative effects, including the loss of the compressive fixation force on the fixation feature 1204 as well as a risk of the implant 1200 coming loose from the fixation bore 210 and migrating into the surrounding body space.

Figure 15:
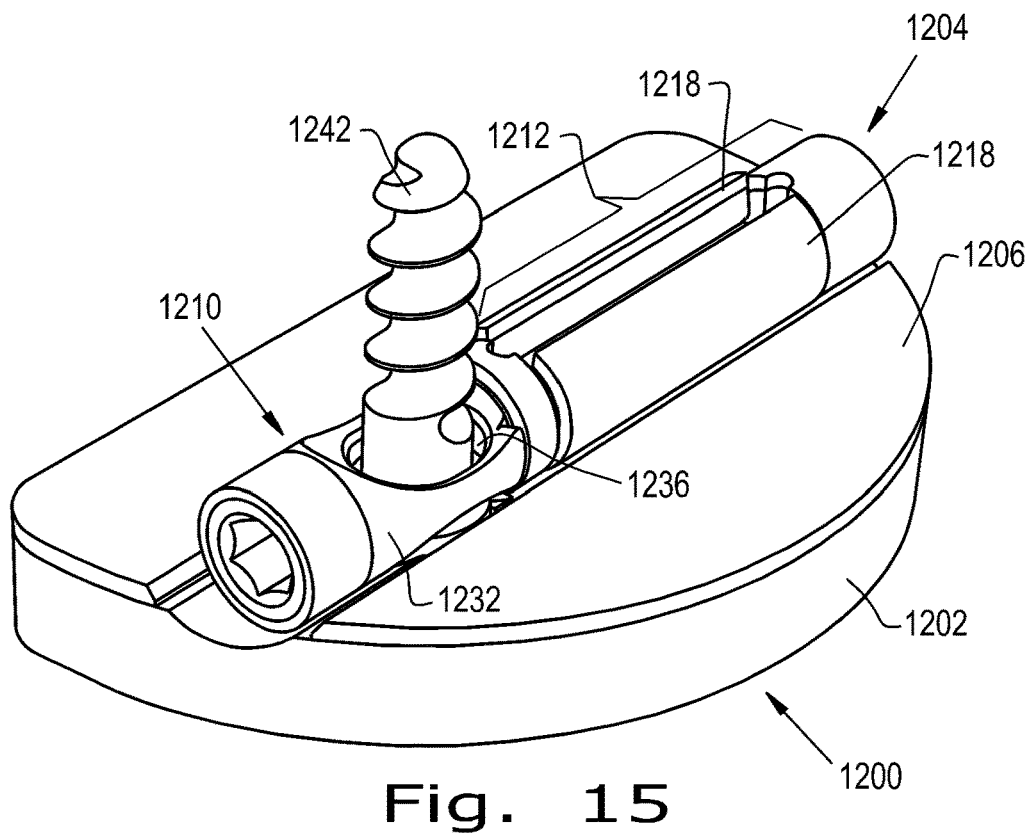
FIG. 15 is a fourth perspective view of the orthopaedic implant of FIG. 12, according to an embodiment of the invention.

To prevent the expandable portion 1212 from being forced back into the non-expanded diameter or width after the expander portion 1208 is turned or rotated, and referring now to FIG. 15, a rotation lock 1242 (e.g., a bone screw) can be inserted through the screw opening (not shown) formed in the implant body 1202 and the opening 1236 formed in a locking portion 1232 of the end segment 1210 of the expander portion 1208. As the screw opening of the implant body and opening 1236 formed in the locking portion 1232 of the end segment 1210 of the expander portion 1208 are aligned only when the expander portion 1208 has been rotated to the proper orientation spreading the expandable portion 1212, there is little risk of a user improperly inserting the bone screw 1242 through the screw opening of the implant body 1202 and into the bone, as material of the locking portion 1232 will prevent the bone screw 1242 from reaching the bone. When the bone screw 1242 is inserted through the aligned openings and screwed into the bone, the abutment of the locking portion 1232 against the bone screw 1242 prevents rotation of the expander portion 1208, and thus the ability of the expandable portion 1208 returning to the non-expanded diameter or width, while the bone screw 1242 also increases fixation of the implant body 1202 to the surface of the bone. Rather than a bone screw 1242, other types of orthopaedic devices can be used as a rotation lock to lock the expandable portion 1212 in the expanded diameter or width, such as pins. Alternatively, the expandable portion 1212 can be locked in the expanded diameter or width by a generic locking mechanism which prevents rotation of the expander portion 1208, rather than a specific orthopaedic device which is implanted into the bone tissue to prevent rotation of the expander portion 1208.

Referring now to FIGS. 16-19, another embodiment of an orthopaedic implant 1600 formed according to the present invention is shown which includes an implant body 1602 having a fixation feature 1604 with an expandable portion 1606 and an expansion bore 1608, an expander portion 1610 configured to expand the expandable portion 1606 from a non-expanded diameter or width to an expanded diameter or width, and a rotation lock 1612 configured to prevent rotation of the expander portion 1610 when the expandable portion 1606 is in the expanded diameter or width orientation. As can be seen, the implant body 1602 can be formed similarly to the previously described implant body, with the addition of an expander guide 1614 which has a guide opening 1616 through which the expander portion 1610 can be inserted to properly align an insertion body 1618 of the expander portion 1610 with the expansion bore 1608 of the expandable portion 1606. As can be seen, the expandable portion 1606 is split into two expandable parts 1620 (i.e., two expandable halves in this embodiment) each having cam surfaces 1220 which can be spread by cams 1622 formed on the insertion body 1618 of the expander portion 1610, similar to the previously described expandable portion 1208. In addition, the expander portion 1610 comprises an end portion 1624 comprising a locking portion 1626 and a keyed portion 1628.

Figure 17:
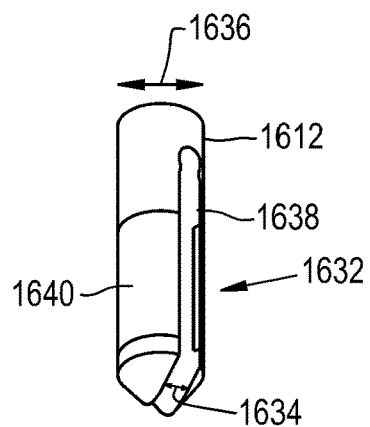
FIG. 17 is a second perspective view of the orthopaedic implant of FIG. 16, according to an embodiment of the invention.
Figure 17:
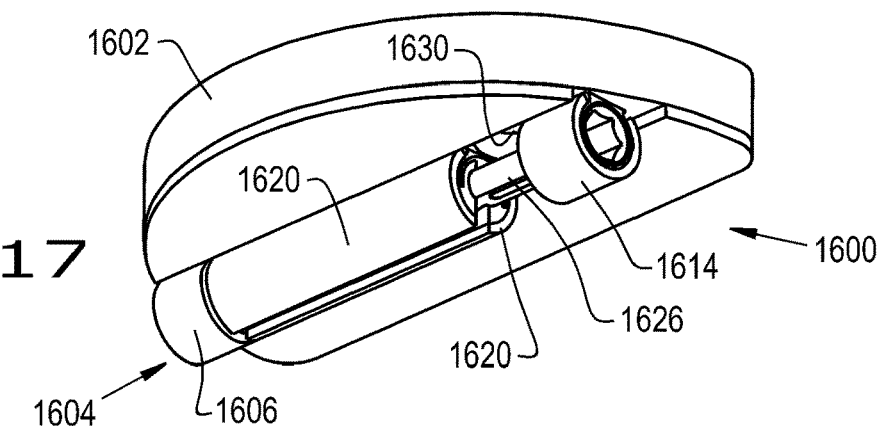

Referring now to FIG. 17, it can be seen that the expander portion 1610 has been inserted through the expander guide 1616 so the insertion body 1618 of the expander portion 1610 is placed within the expansion bore 1608 and the keyed portion 1628 of the end segment 1624 of the expander portion 1610 is placed within the opening 1616 of the expander guide 1614. When placed in this position, the cams 1622 of the insertion body 1618 of the expander portion 1610 are placed within spaces within the expandable portion 1606 so the cams 1622 do not press against the cam surfaces 1220 of the expandable portion 1606 and spread the expandable portion 1606 from the non-expanded diameter or width to the expanded diameter or width prior to turning the expander portion 1610. Further, the locking portion 1626 is aligned with an opening 1630 formed in the implant body 1602. When the insertion body 1602 of the expander portion 1610 is inserted in the expansion bore 1608 in the orientation shown in FIG. 17, the locking portion 1626 is oriented such that a split end portion 1632 of the rotation lock 1612 having a split width 1634 cannot slide over the locking portion 1626, preventing the rotation lock 1612 from being prematurely inserted into an opening (not shown) formed in a bone surface. The locking portion 1626 can thus be dimensioned, for example, to have two dimensions which are perpendicular to one another, and perpendicular to a longitudinal axis of the expander portion 1610, such as a thickness and a width, which are not equal, with one of the dimensions being greater than a split width 1634 of the split end portion 1632 and the other dimension being equal to or less than the split width 1634 of the split end portion 1632. Further, the opening 1630 formed in the implant body 1602 which the rotation lock 1612 extends through can have an opening diameter or width which is substantially the same as a diameter or width 1636 of the rotation lock 1612, the significance of which will be described further herein.

Figure 18:
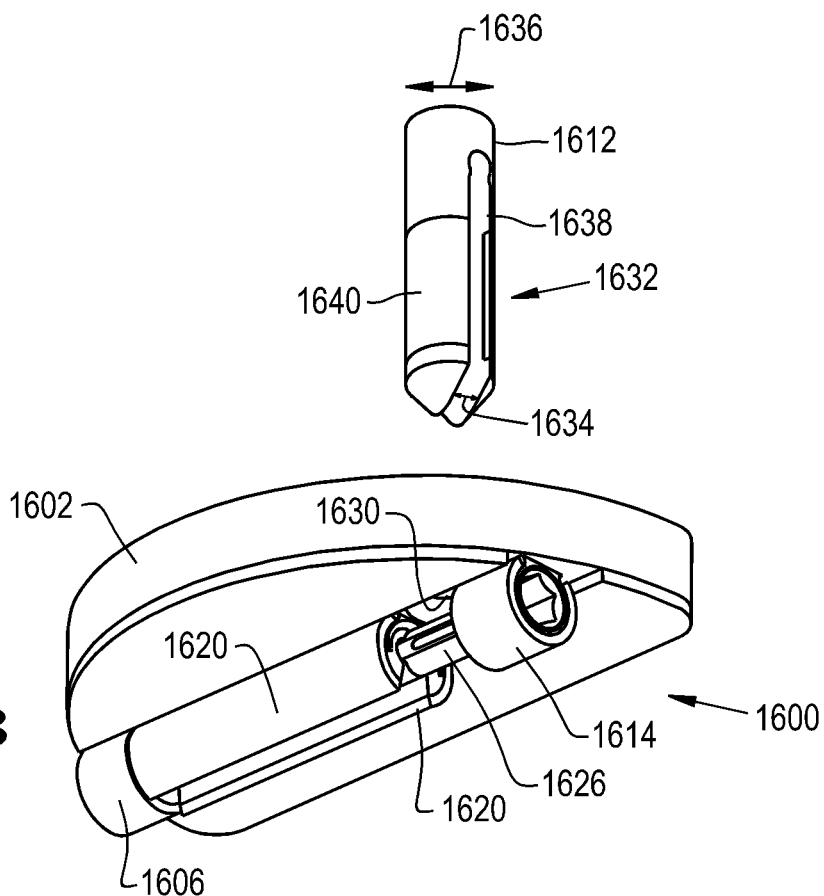
FIG. 18 a third perspective view of the orthopaedic implant of FIG. 16, according to an embodiment of the invention.
Figure 19:
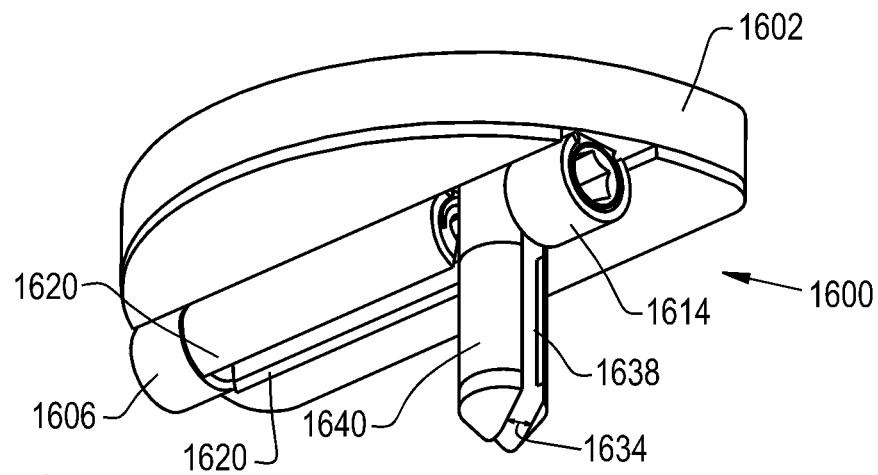
FIG. 19 is a fourth perspective view of the orthopaedic implant of FIG. 16, according to an embodiment of the invention.

Referring specifically now to FIGS. 18-19, it can be seen that the expander portion 1610 has been rotated 90° (or in other embodiments, and angle that is less than 90°) so the cams 1622 of the insertion body 1618 of the expander portion 1610 travel along the cam surfaces 1220 of the expandable portion 1606 and spread the expandable parts 1620 (e.g., halves) so the expandable portion 1606 goes from having the non-expanded diameter or width to the expanded diameter or width. In doing so, the locking portion 1626 of the end segment 1624 of the expander portion 1610 is also oriented such that the dimension aligned with the opening 1630 in the implant body 1602 is equal to or less than the split width 1634 of the split end portion 1632 of the rotation lock 1612. In this orientation, the rotation lock 1612 can be fully placed through the opening 1630 in the implant body 1602 and slide over the locking portion 1626 so the locking portion 1626 abuts against inner walls 1638 of the rotation lock 1612. When the diameter or width 1636 of the rotation lock 1612 is substantially equal to the diameter or width of the opening 1630 in the implant body 1602 holding the rotation lock 1612, sliding the rotation lock 1612 over the locking portion 1626, as shown in FIG. 19, prevents the expandable halves 1620 of the expandable portion 1606 from coming together. Specifically, the expandable halves of the expandable portion coming together requires rotation of the expander portion, which would cause spreading of the split end portion of the rotation lock. Such spreading of the split end portion 1632 is prevented by outer walls 1640 of the rotation lock 1612 abutting against walls of the opening 1630 formed in the implant body 1602, and therefore the expander portion 1610 is prevented from rotating and the expandable halves 1620 are prevented from coming together. As can be seen, the rotation lock 1612 can be, for example, a split post (e.g., a pin with a split end portion) which will be placed in an opening formed in a prepared bone surface to properly orient the implant during implantation. The split post can also have, if desired, ingrowth material placed thereon to provide additional fixation during implantation. It should thus be appreciated that the rotation lock 1612 can be formed in a variety of ways in order to prevent the expandable portion 1620 from returning to the non-expanded diameter or width once the expander portion 1610 has been rotated to the expanding orientation, and the embodiment shown in FIGS. 16-19 is only one possible configuration.

Figure 20:
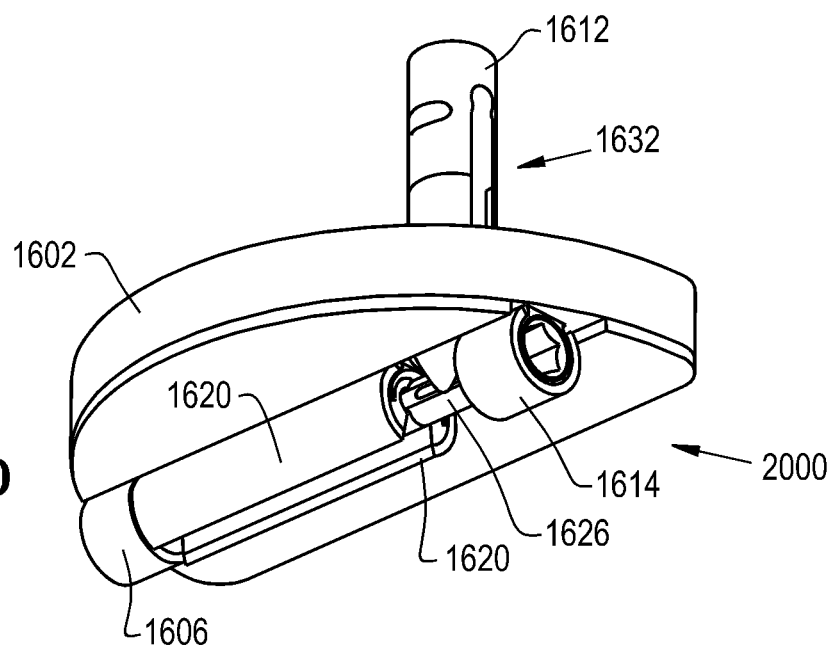
FIG. 20 is a first perspective view of an orthopaedic implant, according to another embodiment of the invention.
Figure 21:
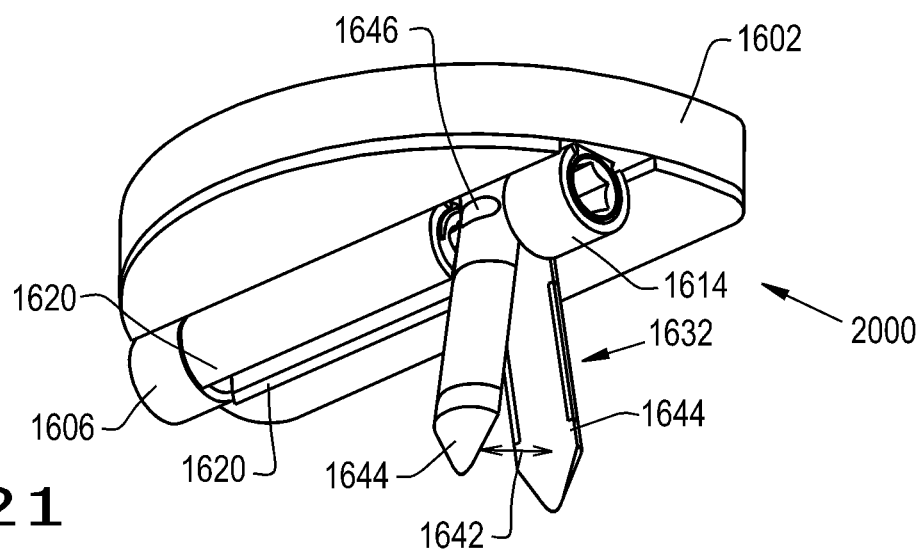
FIG. 21 is a second perspective view of the orthopaedic implant of FIG. 20, according to an embodiment of the invention.
Figure 22:
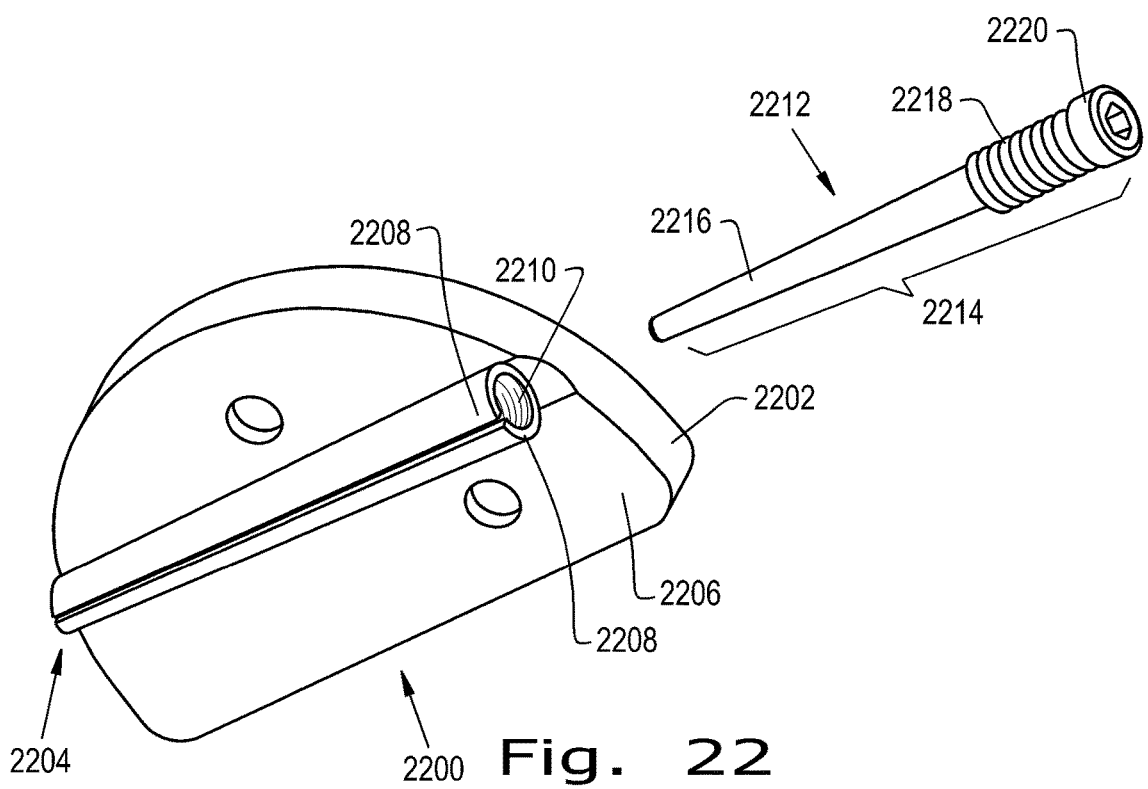
FIG. 22 is a first perspective view of an orthopaedic implant, according to another embodiment of the invention.

Referring now to FIGS. 20-21, an alternative embodiment 2000 of the orthopaedic implant shown in FIGS. 16-19 is shown which has a rotation lock 1612 with a split end portion 1632 having a split width which is less than the dimension of the locking portion 1626 of the end segment 1624 of the expander portion 1610 aligned with the opening 1630 formed in the implant body 1602 when the expander portion 1610 is rotated to expand the expandable portion 1606. As the split width of the split end portion of the rotation lock 1612 is less than the aligned dimension of the locking portion 1626, the split width of the rotation lock increases as the rotation lock 1612 slides across the locking portion 1626 to result in split width 1642 of the completely split orientation of the rotation lock 1612 shown in FIG. 21. By having the rotation lock 1612 split in this manner, each split portion 1644 of the split end portion 1632 of the rotation lock 1612 can press tightly against walls of a bore (not shown) formed in the bone surface as the rotation lock 1612 is inserted into the bore. The rotation lock can then be locked into position, for example, by placing a pin (not shown) through aligned openings 1646 formed in the rotation lock 1612 and the locking portion 1626 of the expander portion 1610.

Figure 23:
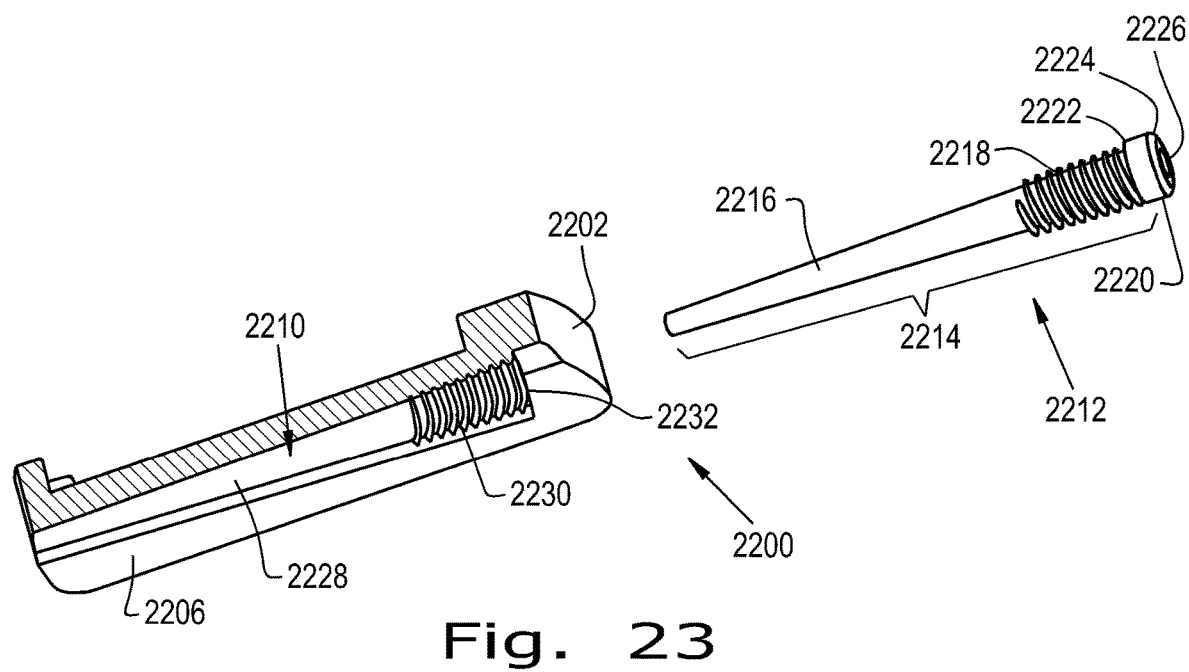
FIG. 23 is a second perspective view of the orthopaedic implant of FIG. 22, according to an embodiment of the invention.
Figure 24:
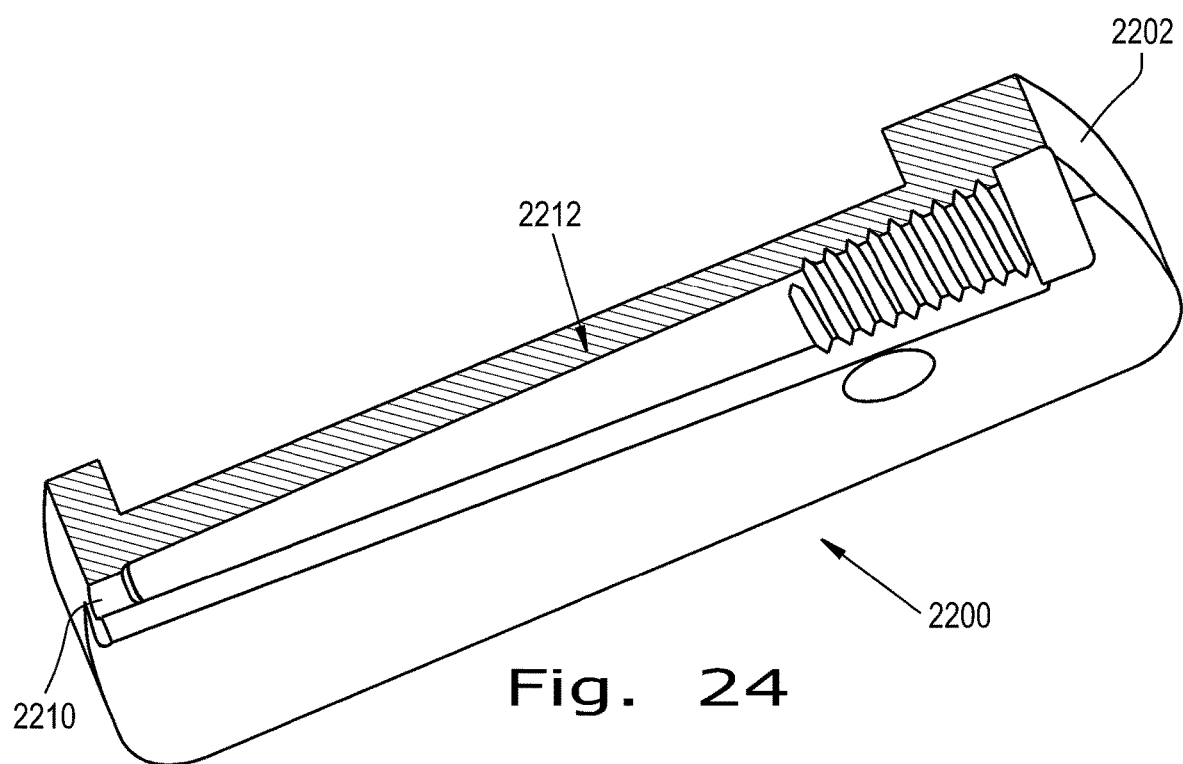
FIG. 24 is a third perspective view of the orthopaedic implant of FIG. 22, according to an embodiment of the invention.
Figure 25:
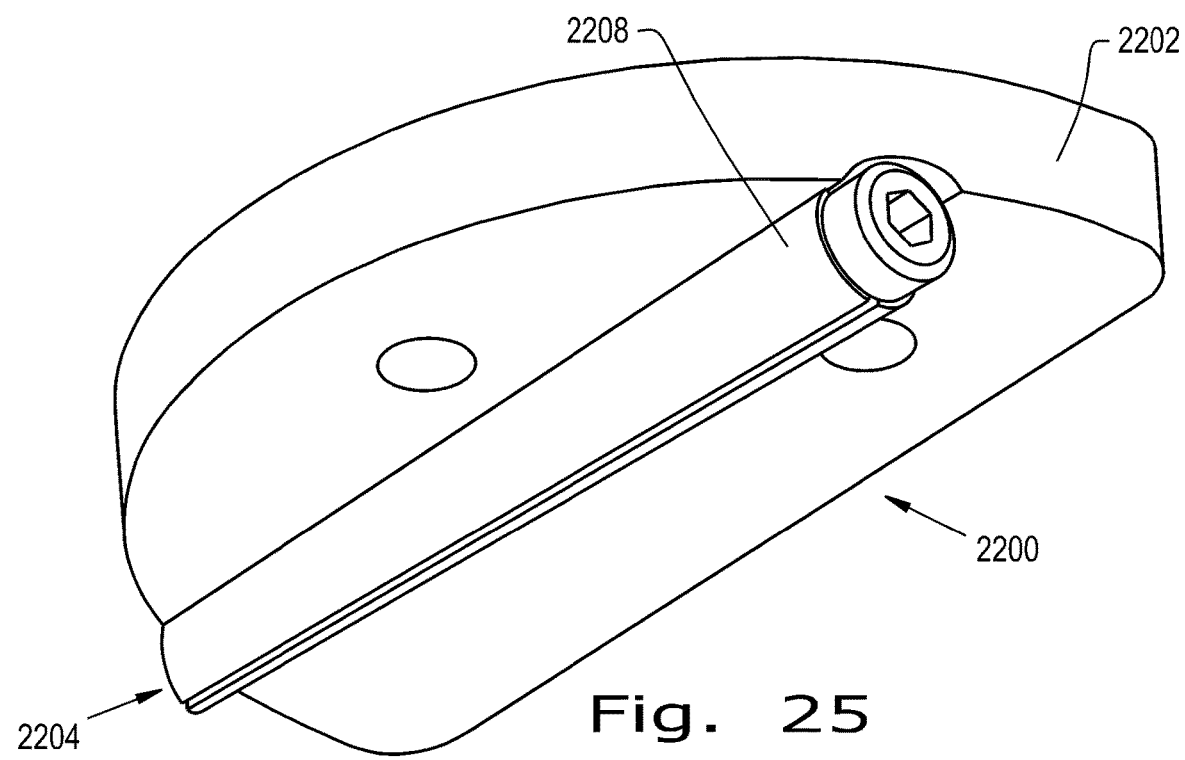
FIG. 25 is a fourth perspective view of the orthopaedic implant of FIG. 22, according to an embodiment of the invention.

Referring now to FIGS. 22-25, yet another embodiment of an orthopaedic implant 2200 formed according to the present invention is shown. The orthopaedic implant 2200 comprises an implant body 2202 which can be configured to be implanted in a tibia, similar to previously described implant bodies. The implant body 2202 can have an expandable fixation feature 2204 on a bottom surface 2206 of the implant body 2202 which includes two tapered expandable halves 2208 defining a tapered expansion bore 2210 therebetween. The implant 2200 can also include an expander 2212 which has a tapered portion 2214 comprising an elongated conical shape with a smooth, unthreaded portion 2216 and a threaded end portion 2218, and a keyed portion 2220, which may or may not be tapered, having a first end 2222 coupled to the threaded end portion 2218 and a second end 2224 which has a socket 2226 for receiving a tool to rotate the expander 2212. While the expander 2212 is shown as having an elongated conical shape, i.e., a diameter that increases along a length from the unthreaded portion 2216 to the keyed portion 2220, the expander 2212 can have other shapes, if desired, and it is not necessary that the threaded end portion 2218 has a larger diameter or width than the unthreaded portion 2216. As shown in FIG. 23, the expansion bore 2210 can also have a tapered diameter or width along with a smooth bore portion 2228 and a threaded bore portion 2230 adjacent an entrance 2232 of the expansion bore 2210. At least a portion of the expander 2212 can have a greater diameter or width than a maximum diameter or width of the expansion bore 2210. To expand the expanding fixation feature, the expander 2212 can slide into the expansion bore 2210. Once a portion of the expander 2212 advances to a portion of the expansion bore 2210 with a smaller diameter or width, further advancement of the expander 2212 in the expansion bore 2210 will cause the expandable halves 2208 of the fixation feature 2204 to spread apart, causing expansion of the fixation feature 2204. This point can be, for example, when the threaded end portion 2218 of the expander 2212 engages the threaded portion 2230 of the expansion bore 2210. To expand the expandable halves 2208, the expander 2212 can be rotated, via a tool inserted into the socket 2226 of the keyed portion 2220, for example, to further advance the expander 2212 in the expansion bore 2210 and cause expansion of the fixation feature 2204. Once the expander 2212 fully resides within the fixation feature 2204, as shown in FIGS. 24-25, the fixation feature 2204 is fully expanded and can help fixate the implant body 2202 in a fixation bore 210 formed in a resected bone surface 208, as previously described. As it may be desired to remove the implant body 2202 or have the fixation feature 2204 return to a non-expanded diameter or width, the first end 2222 of the keyed portion 2220 of the expander 2212 can have an end diameter or width which is greater than an expanded diameter or width of the expansion bore 2210, so the keyed portion 2220 cannot advance into the expansion bore 2210. This sizing can prevent the expander 2212 from being advanced into the expansion bore 2210 and being inaccessible after the implant 2200 has been implanted. It should therefore be appreciated that various types of expanders can be utilized according to the present invention which expand a fixation feature 2204 of an orthopaedic implant 2200 by threading to threads 2230 of an expansion bore 2210, locking the fixation feature 2204 in the expanded state in the process.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An orthopaedic implant, comprising:
    an implant body having a first surface and a second surface opposite the first surface, the second surface including a fixation feature and a planar portion, the fixation feature configured to have a variable width for fastening the implant to a fixation bore formed in a bone, the implant body being D-shaped having a straight edge and a curved edge, a length of the fixation feature being parallel to the straight edge of the implant body, the fixation feature being configured to have a width that tapers along the length of the fixation feature, wherein the width is defined in a direction that extends from the straight edge to the curved edge, the curved edge of the implant includes a first edge segment and a second edge segment opposing the first edge segment, the fixation feature extending from the first edge segment to the second edge segment, the fixation feature includes a rounded outer surface for reception by the fixation bore, the rounded outer surface being directly connected to the planar portion of the second surface such that the fixation feature has only a partially round configuration, the fixation feature having a circular cross-section that intersects with the planar portion of the second surface such that the circular cross-section is only partially circular, the fixation feature having an absence of an element that projects radially beyond the circular cross-section, the first edge segment and the second edge segment being spaced apart entirely from the straight edge, the implant body further including a recess formed in the first surface for receiving a removable articulating insert; and
    a suture anchor, the implant body further including a first opening extending from the recess to the second surface, the suture anchor being mounted to, being housed by, and extending below the first opening, the suture anchor including a body including a top, a bottom, and a second opening extending longitudinally through the body from the top to the bottom and concentrically with the first opening, the suture anchor being configured for a suture extending through the second opening and thus also through the first opening.

2. The orthopaedic implant according to claim 1, wherein the bone is a tibia.

3. The orthopaedic implant according to claim 1, wherein a portion of the second surface is configured to form the fixation feature.

4. The orthopaedic implant according to claim 1, wherein the fixation feature has a flat surface opposite the rounded outer surface, the flat surface being attached to the second surface.

5. The orthopaedic implant according to claim 1, wherein the fixation bore has a constant width and a length equal to the length of the fixation feature, wherein the widths of the fixation feature at positions along the length of at least a portion of the fixation feature are greater than the constant width of the fixation bore at corresponding positions along the length of the fixation bore.

6. The orthopaedic implant according to claim 1, wherein the fixation bore has a width that varies along a length of the fixation bore, the length of the fixation bore equal to the length of the fixation feature, wherein the widths of the fixation feature at positions along the length of at least a portion of the fixation feature are greater than the widths of the fixation bore at corresponding positions along the length of the fixation bore.

7. The orthopaedic implant according to claim 1, wherein the first surface is an articulating surface.

8. The orthopaedic implant according to claim 1, wherein the fixation feature includes a first longitudinal edge and a second longitudinal edge opposing the first longitudinal edge, the first longitudinal edge of the fixation feature being aligned with the first edge segment of the curved edge of the implant, and the second longitudinal edge of the fixation feature being aligned with the second edge segment of the curved edge of the implant.

9. The orthopaedic implant according to claim 1, wherein the first surface further includes a projection projecting over the recess.

* * * * *